(12) United States Patent
Ohishi et al.

(10) Patent No.: US 7,170,591 B2
(45) Date of Patent: Jan. 30, 2007

(54) BLOOD TREATMENT DEVICE AND METHOD FOR BLOOD TREATMENT

(75) Inventors: Takayuki Ohishi, Shizuoka (JP); Yoshihiro Mori, Shizuoka (JP)

(73) Assignee: Nikkiso Co. Ltd., Tokyo (JP)

( * ) Notice: Subject to any disclaimer, the term of this patent is extended or adjusted under 35 U.S.C. 154(b) by 339 days.

(21) Appl. No.: 10/623,141

(22) Filed: Jul. 18, 2003

(65) Prior Publication Data

US 2004/0057037 A1    Mar. 25, 2004

(30) Foreign Application Priority Data

Jul. 18, 2002   (JP)   ............................. 2002-209331
May 9, 2003    (JP)   ............................. 2003-132110

(51) Int. Cl.
*G01N 33/48*   (2006.01)

(52) U.S. Cl. ...................... 356/39; 604/4.01; 604/6.08

(58) Field of Classification Search .................. 356/39
See application file for complete search history.

(56) References Cited

U.S. PATENT DOCUMENTS

| | | | | |
|---|---|---|---|---|
| 5,601,080 | A * | 2/1997 | Oppenheimer | 356/39 |
| 5,830,133 | A * | 11/1998 | Osten et al. | 356/39 |
| 5,956,130 | A * | 9/1999 | Vancaillie et al. | 356/39 |
| 6,126,612 | A * | 10/2000 | Roizen et al. | 356/39 |
| 6,304,767 | B1 * | 10/2001 | Soller et al. | 356/39 |
| 6,413,233 | B1 * | 7/2002 | Sites et al. | 604/4.01 |
| 6,794,194 | B2 * | 9/2004 | Fava et al. | 356/39 |
| 6,806,947 | B1 * | 10/2004 | Ekdahl et al. | 356/39 |

FOREIGN PATENT DOCUMENTS

| | | |
|---|---|---|
| JP | 62251662 | 11/1987 |
| JP | 11 221275 | 8/1999 |
| JP | 11 226119 A | 8/1999 |
| JP | 2001-540 | 1/2001 |
| JP | 2002-165876 A | 6/2002 |
| JP | 2002-165877 A | 6/2002 |
| JP | 2004-097781 A | 4/2004 |

* cited by examiner

*Primary Examiner*—Gregory J. Toatley, Jr.
*Assistant Examiner*—Juan D. Valentin, II
(74) *Attorney, Agent, or Firm*—Darby & Darby (57) ABSTRACT

The present invention provides a blood treatment device and methods of blood treatment to provide an individual patient with the most suitable blood treatment and reduced treatment duration. Specifically, the invention provides a blood treatment device comprising a treating means 11 that treats blood collected from a patient; a measuring means 12 that measures parameters of the patient's blood and indicates blood condition; a controlling means 13 that controls the treatment procedures based upon the blood parameters; a storing means 15 that records an ideal patient-specific blood parameter curve for the treatment duration; and a directing means 14 that directs the control by the controlling means 13 so that the measured blood parameters approximate to the ideal blood parameter curve by comparing the measured blood parameters with the ideal blood parameter curve recorded by the storing means 15.

19 Claims, 7 Drawing Sheets

BLOOD TREATMENT DEVICE AND METHOD FOR BLOOD TREATMENT

BACKGROUND OF THE INVENTION

The present invention relates to a blood treatment device which collects blood from a patient and a method for blood treatment.

In dialysis treatments, a blood circuit consisting mainly of flexible tubing is used to place the blood of a patient in extracorporeal blood circulation. This blood circuit arrangement includes an arterial blood circuit having an arterial needle at one end to collect the blood from the patient and a venous blood circuit having a venous needle at one end to return the blood to the patient. A dialyzer can be incorporated between the arterial blood circuit and the venous blood circuit.

A roller blood pump is placed in the arterial blood circuit. By driving the pump, the blood of the patient is collected through the arterial needle and flows extracorporeally through the arterial blood circuit, the dialyzer, and the venous blood circuit. There are multiple hollow fibers inside the dialyzer. The blood flows through each hollow fiber.

Two projections are formed on the dialyzer case, one being a dialyzing fluid inlet port and the other being a dialyzing fluid outlet port. Dialyzing fluid of predetermined concentration is supplied in through the dialyzing fluid inlet port, along the outside of the hollow fibers (i.e., between the outside surface of the hollow fibers and the inside surface of the dialyzer case), and then out through the dialyzing fluid outlet port.

The walls of hollow fibers, which contain micropores, form blood purifying membranes. Waste products of the blood passing through the inside of the hollow fibers are dialyzed to the dialyzing fluid through the blood purifying membrane and the purified blood returns to the patient. To remove water from the blood of the patient during the dialysis treatment, the dialysis device includes a ultrafiltration pump.

The amount of water to be removed (water removal rate) is regulated by controlling the driving speed of the ultrafiltration pump. However, if too much water is removed or if water is removed too quickly, the volume of the circulating blood of the patient is excessively reduced such that blood pressure drop or shock may be induced. On the other hand, if the water removal rate is too low, the treatment duration may be prolonged and the burden to the patient can be too great.

Therefore, as disclosed in Japanese laid open patent publication number Hei 11-221275 and Japanese laid open patent publication number 2001-540, there are blood treatment devices that control the rate of water removal while monitoring the condition of the patient. These existing blood treatment devices have used hematocrit values and other blood parameters to monitor the condition of a patient's blood. The hematocrit value is an indicator of blood concentration, and is expressed as the ratio of red blood cell volume to whole blood volume.

The aforementioned blood treatment devices measure the hematocrit value of the patient in real-time when the patient is undergoing water removal, and can control the water removal rate based on the hematocrit value. This control prevents the drop in blood pressure or the shock caused by excessive reduction in the patient's blood volume. More particularly, numerous zones for hematocrit values are set beforehand and the rate of water removal is controlled according to the zone in which the measured hematocrit value belongs.

Although numerous zones were set beforehand for hematocrit values in the aforementioned conventional blood treatment devices and the rate of water removal was controlled according to the zone in which the measured hematocrit value belonged, the zone setting was not necessarily suitable for the individual patient and it was possible that some patients could experience complications.

Individual patients have different hematocrit values at which the patient feels ill, and it is impossible to set a standard hematocrit value for all patients. Therefore, the water removal rate suitable for one patient may not be suitable for another patient who feels ill at that particular rate. Furthermore, the aforementioned conventional technologies not only control the water removal rate, but also other blood treatments such as fluid substitution. Similarly, these other blood treatments may also be unsuitable for all patients.

OBJECT AND SUMMARY OF THE INVENTION

The object of the present invention is to overcome the problems of the aforementioned blood treatment devices and to provide a blood treatment device and methods of blood treatment that can carry out the most suitable blood treatment for an individual patient while also reducing treatment duration at the same time.

One embodiment of the invention provides a blood treatment device comprising: a treating means that treats blood collected from a patient, according to set treatment procedures; a measuring means that measures parameters of the blood of the patient whereby the condition of the blood is determined; a controlling means that controls the treatment procedures based on the blood parameters measured by the measuring means; a storing means that records an ideal patient-specific blood parameter curve for the treatment duration; and a directing means that directs the change of control by the controlling means by comparing the ideal blood parameter curve recorded by the storing means with the measured blood parameters so that the measured blood parameters approximate to the ideal blood parameter curve such that the patient is treated by the set treatment procedures.

Another embodiment of the invention provides the blood treatment device as above, wherein the measured blood parameter is the hematocrit value that reflects blood concentration or can be used to calculate the rate of change in the circulating blood volume.

Another embodiment of the invention provides a blood treatment device as one of the above devices, wherein the treating means comprises a driving means of a blood purifying apparatus, which purifies the blood of a patient while extracorporeally circulating the blood. Additionally, the controlling means controls one of the following, or a combination of two or more of the following, set treatment procedures: water removal rate; blood flow rate; fluid substitution rate; concentration of dialyzing fluid; sodium ion concentration; time for blood treatment; flow rate of dialyzing fluid; temperature of dialyzing fluid; volume of substitution fluid; amount of drug injected; and rate of drug injection.

Another embodiment of the invention provides a blood treatment device as any one of the above devices, wherein the ideal blood parameter curve is corrected based on the blood parameters measured at the start of blood treatment by the measuring means.

Another embodiment of the invention provides a blood treatment device as any one of the above devices, wherein the directing means varies a change in control of said controlling means based on a deviation between the ideal blood parameter curve and the blood parameter measured by the measuring means.

Another embodiment of the invention provides a blood treatment device as any one of the above devices, wherein the ideal blood parameter curve is an approximation calculated on the basis of the ideal blood parameter curve obtained when the blood treatment is carried out before this dialysis treatment.

Another embodiment of the invention provides a blood treatment device as any one of the above devices, wherein, when the blood parameters measured by the measuring means undergo a drastic change, the direction to change by the directing means is overridden in such a way as to suppress the drastic change.

Another embodiment of the invention provides a blood treatment device as any one of the above devices, wherein the treatment duration is one of the parameters considered when the directing means directs the controlling means to change the treatment procedures.

Another embodiment of the invention provides a blood treatment device as any one of the above devices, wherein the absolute base line is established against the blood parameters, such that when the blood parameters drop below the base line, the direction to change by the directing means is overridden in order to control the treating means.

Another embodiment of the invention provides a blood treatment method using a blood treatment device comprising: a treating means that treats blood collected from a patient according to set treatment procedures; a measuring means that measures parameters of the patient's blood whereby the condition of the blood is determined; and a controlling means that controls the treatment procedures based upon the blood parameters measured by the measuring means, wherein an ideal patient-specific blood parameter curve for the treatment duration is obtained beforehand, and when the patient is treated by the treating means according to the set treatment procedures, the controlling means changes the control so that blood parameters measured by the measuring means approximate to the ideal blood parameter curve.

Another embodiment of the invention provides a blood treatment method as above, wherein the blood parameter is the hematocrit value that reflects the concentration of blood or is used to calculate the rate of change in the circulating blood volume.

Another embodiment of the invention provides a blood treatment method as one of the above methods, wherein the treating means comprises a driving means of a blood purifying apparatus that purifies the blood of a patient while extracorporeally circulating the blood. Additionally, the controlling means controls one of the following, or a combination of two or more of the following, set treatment procedures: water removal rate; blood flow rate; fluid substitution rate; concentration of dialyzing fluid; sodium ion concentration; time for blood treatment; flow rate of dialyzing fluid; temperature of dialyzing fluid; volume of substitution fluid; amount of drug injected; and rate of drug injection.

Another embodiment of the invention provides a blood treatment method as in any one of the above methods, wherein the ideal blood parameter curve is corrected based on the blood parameters measured at the start of blood treatment by the measuring means.

Another embodiment of the invention provides a blood treatment method as in any one of the above methods, wherein the change in control by the controlling means is based on the deviation of the blood parameters measured by the measuring means from the ideal blood parameter curve.

Another embodiment of the invention provides a blood treatment method as in any one of the above methods, wherein an approximation formula is calculated based on the ideal blood parameter curve, which was obtained beforehand. The controlling means then controls the blood condition such that the blood parameters measured by the measuring means approximate to the ideal blood parameter curve.

Another embodiment of the invention provides a blood treatment method as in any one of the above methods, wherein, when the blood parameters measured by the measuring means undergo a drastic change, the controlling means suppresses the change by overriding its function to approximate to the ideal blood parameter curve.

Another embodiment of the invention provides a blood treatment method as in any one of the above methods, wherein the treatment duration is one of the parameters that approximates to the ideal blood parameter curve.

Another embodiment of the invention provides a blood treatment method as in any one of the above methods, wherein the absolute base line is established against the blood parameters, such that when the blood parameters drop below the base line, the function of the treating means to approximate to the ideal blood parameter curve is overridden.

LIST OF REFERENCE NUMERALS

1 blood circuit; 1*a* arterial blood circuit; 1*b* venous blood circuit; 2 dialyzer; 2*a* blood inlet port; 2*b* blood outlet port; 2*c* dialyzing fluid inlet port; 2*d* dialyzing fluid outlet port; 3 blood pump; 4 drip chamber; 5 air bubble detector; 6 dialysis monitor; 7 hematocrit sensor; 8 ultrafiltration pump; 9 heater; 10 deaeration unit; 11 treating means; 12 measuring means; 13 controlling means; 14 directing means; 15 storing means; a arterial needle; b venous needle; L1 dialyzing fluid inlet line; L2 dialyzing fluid outlet line; L3 bypass line; P duplex pump; A ideal blood parameter curve; B lower limit curve; C upper limit curve; D measured curve.

DETAILED DESCRIPTION OF THE PREFERRED EMBODIMENTS

The embodiments of the present invention are explained using the figures. The blood treatment device according to one embodiment includes a blood purifying apparatus that purifies the blood of a patient by extracorporeal circulation. The blood purifying apparatus includes: a blood circuit to which a dialyzer is connected, a dialysis monitor, which supplies dialyzing fluid to the dialyzer, and a dialyzing fluid supplier that prepares dialyzing fluid.

Figure 1:
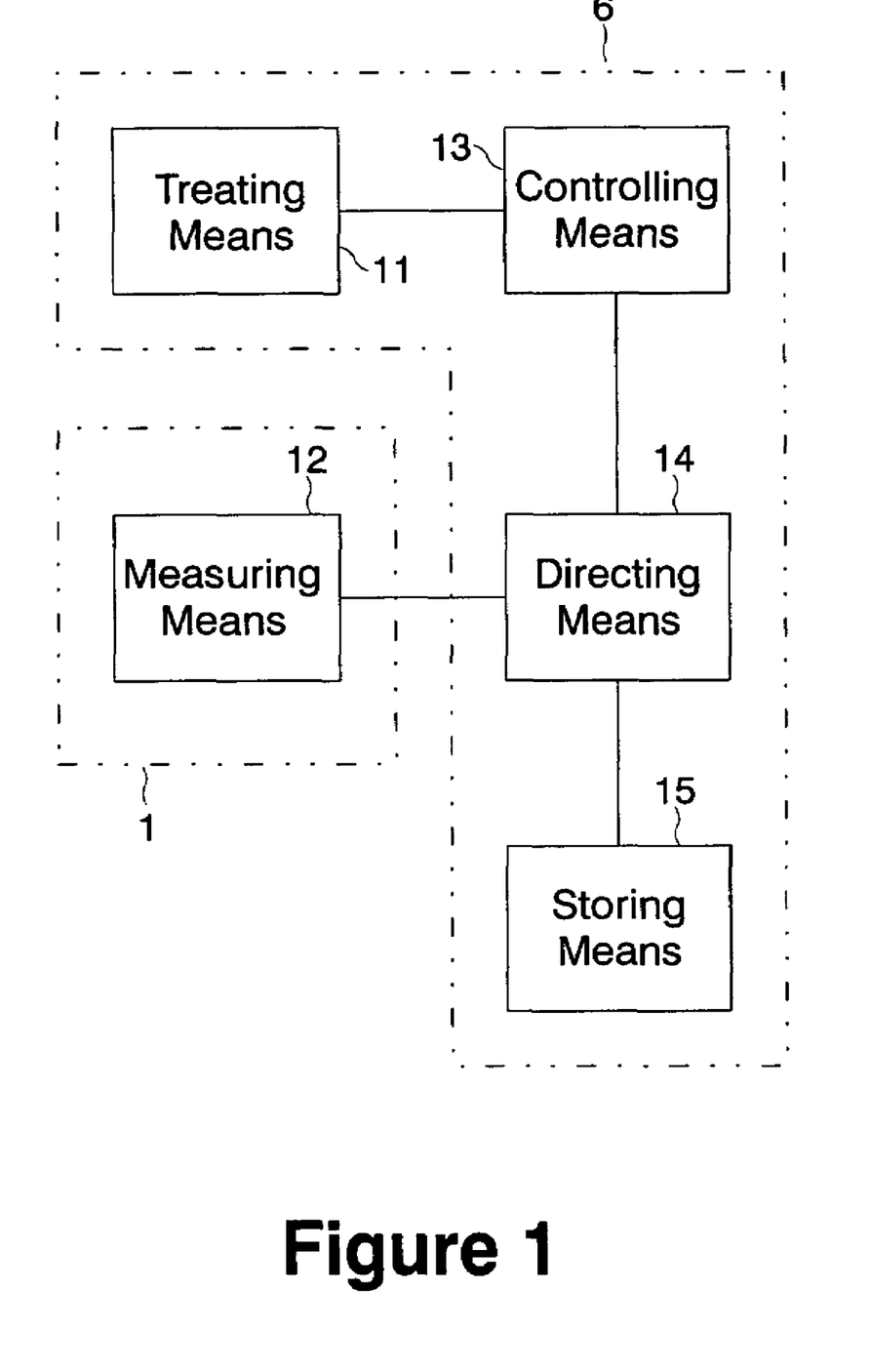
FIG. 1 is a block diagram of the blood treatment device of the present invention.

The blood purifying apparatus, as shown in FIG. 1, includes a treating means 11 that performs predetermined treatment procedures on the blood of the patient, a measuring means 12 that measures the hematocrit value as a blood parameter that is related to the condition of the blood of the patient, a controlling means 13 that controls the treatment procedures based on the hematocrit value measured by the measuring means, a directing means 14, and a storing means 15.

Figure 2:
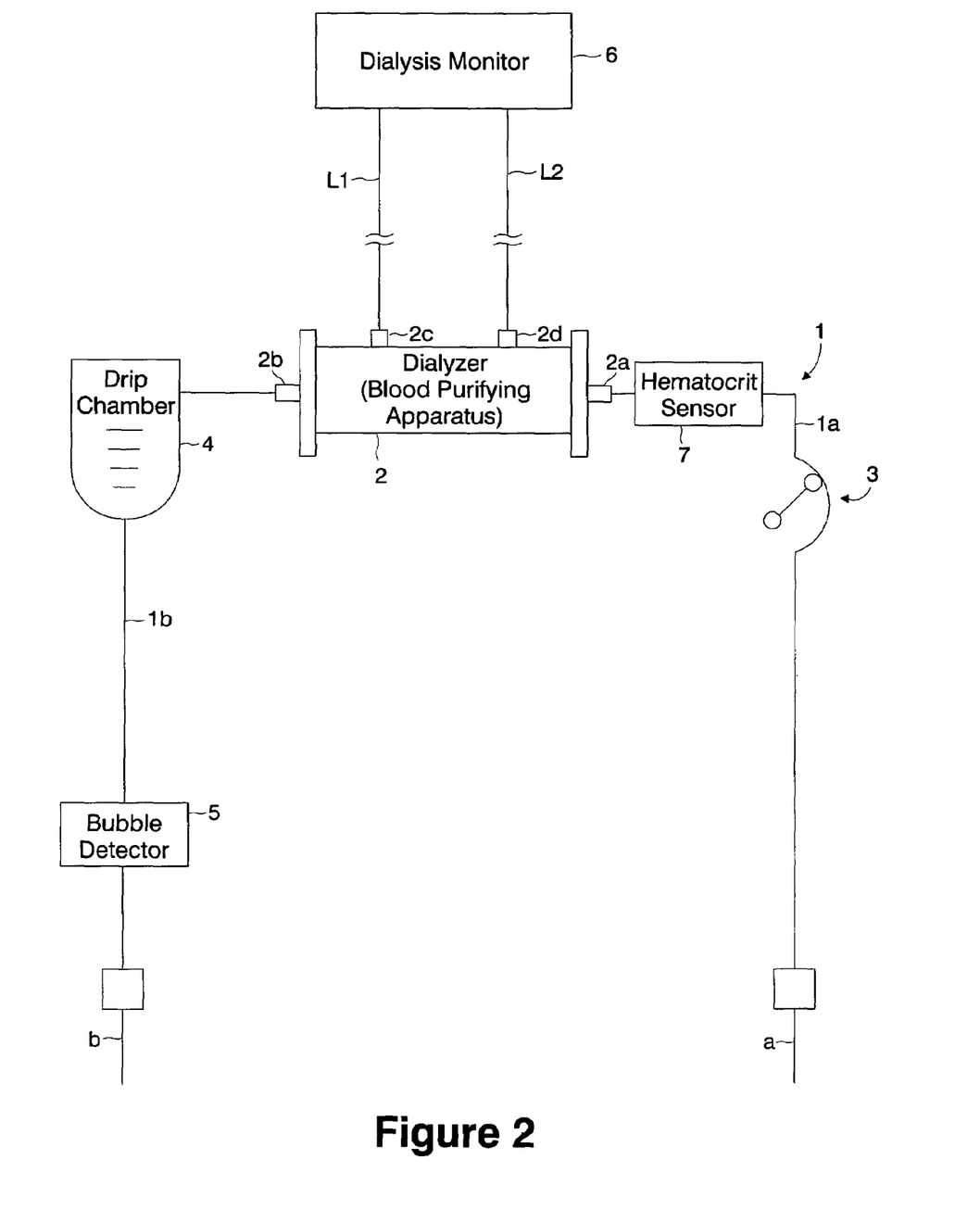
FIG. 2 is a schematic diagram of the blood circuit and dialysis monitor to which the blood treatment device of the present invention is applied.

The blood circuit 1 as shown in FIG. 2 includes an arterial blood circuit 1a and a venous blood circuit 1b, which are made from flexible tubing. A dialyzer 2 acts as a blood purifying apparatus and is connected between the arterial blood circuit 1a and the venous blood circuit 1b.

An arterial needle a is attached to the end of the arterial blood circuit 1a, and a blood pump 3 is attached in the middle of the arterial blood circuit 1a. A venous needle b is attached to the end of the venous blood circuit 1b, and a drip chamber 4 is attached in the middle of the venous blood circuit 1b.

When the blood pump 3 is driven while the arterial needle a and the venous needle b are affixed to the patient, the blood of the patient flows through the arterial blood circuit 1a and into the dialyzer 2. The dialyzer 2 purifies the blood, and air bubbles are removed by the drip chamber. The blood flows out of the dialzyer 2 through the venous blood circuit 1b and returns to the body of the patient. Thus, the blood of the patient is purified by the dialyzer 2 while extracorporeally circulating through the blood circuit 1.

Further, a air bubble detector 5 is placed near the venous needle b in the venous blood circuit 1b. The air bubble detector 5 monitors the presence of air in the blood flowing through the venous blood circuit 1b and can, for example, be formed from a sensor that detects air by applying ultrasound to the flexible tubing.

Several ports are located on the dialyzer case: a blood inlet port 2a, a blood outlet port 2b, a dialyzing fluid inlet port 2c, and a dialyzing fluid outlet port 2d. The blood inlet port 2a and the blood outlet port 2b are connected to the arterial blood circuit 1a and venous blood circuit 1b, respectively. The dialyzing fluid inlet port 2c and the dialyzing fluid outlet port 2d are connected to a dialyzing fluid inlet line L1 and a dialyzing fluid outlet line L2, respectively. Lines L1 and L2 extend from a dialysis monitor 6.

The dialyzer 2 includes multiple hollow fibers. The blood flows inside of the hollow fibers and the dialyzing fluid flows between the outside surface of the hollow fibers and the inside surface of the dialyzer case. The hollow fibers include many micropores that are located in the outside and the inside surfaces of the hollow fiber membrane, and through which waste products in the blood are dialyzed to the dialyzing fluid.

Figure 3:
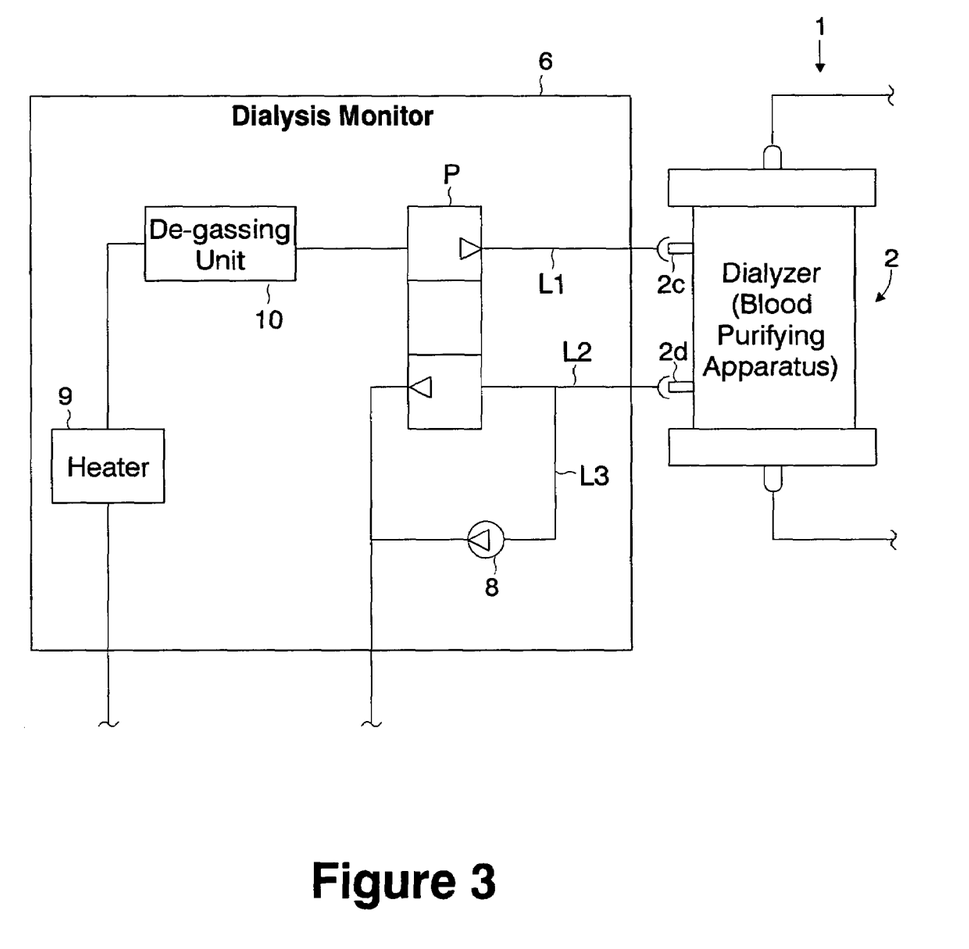
FIG. 3 is a schematic diagram of the dialysis monitor connected to the blood circuit to which the blood treatment device of the present invention is applied.

Further, as shown in FIG. 3, the dialysis monitor 6 includes a duplex pump P that is connected between the dialyzing fluid inlet line L1 and the dialyzing fluid outlet line L2. A bypass line L3 is connected to the dialyzing fluid outlet line L2, and bypasses the duplex pump P. A ultrafiltration pump 8 is connected to the bypass line L3. Additionally, a first end of the dialyzing fluid inlet line L1 is connected to the dialyzer 2 at the dialyzing fluid inlet port 2c. A second end of the dialyzing fluid inlet line L1 is connected to a dialyzing fluid supplier (not shown), which prepares the dialyzing fluid of predetermined concentration.

A first end of dialyzing fluid outlet line L2 is connected to the dialyzer 2 at the dialyzing fluid outlet port 2d. A second end of dialyzing fluid outlet line L2 is connected to a waste fluid disposal means (not shown).

The dialyzing fluid supplied from the dialyzing fluid supplier passes through the dialyzing fluid inlet line L1 to the dialyzer 2, the passes through the dialyzing fluid outlet line L2 and the bypass line L3, and is let out to the waste fluid disposal means. In FIG. 3, the numerals 9 and 10 indicate a heater and a deaeration unit that are both connected to the dialyzing fluid inlet line L1.

The ultrafiltration pump 8 removes water from the blood of the patient flowing through the dialyzer 2. When the ultrafiltration pump is activated, the volume of dialyzing fluid let out of the dialyzing fluid outlet line L2 becomes greater than that of dialyzing fluid introduced from the dialyzing fluid inlet L1, and water is removed from the blood by the difference of the inlet and outlet volumes.

The ultrafiltration pump 8 constitutes a treating means 11 in the present invention. As shown in FIG. 1, the ultrafiltration pump 8 (treating means 11) is connected electrically to a controlling means 13 and the operating rate (the water removal rate) is controlled by the controlling means.

The initial water removal rate is set as the total water removal volume divided by the water removal time. After the water removal is started at this rate, the ultrafiltration pump 8 is controlled by the controlling means 13 based on the blood parameter curve recorded by the storing means 15, which is described later. Incidentally, the total water removal volume and water removal time, especially the former, often differ in each dialysis treatment. Therefore, the initial water removal rate is set anew for each dialysis treatment.

Measuring means 12 includes a hematocrit sensor 7, which is connected to the arterial blood circuit 1a in the blood circuit 1. The hematocrit sensor 7, for example, contains a photo emitter, such as a light emitting diode (LED), and a photo detector, such as a photo diode, and measures the hematocrit value that reflects the concentration of the patient's blood flowing through the blood circuit 1 by emitting light (for example, near-infrared light of 805±15 nm wave length) toward the blood while at the same time detecting either pass-through or reflected light by the photo detector.

Furthermore, the hematocrit value, which reflects the blood concentration, is obtained from the electronic signal output from the photo detector. The hematocrit value can be obtained by quantifying the red blood cells electronically based on the fact that blood components, such as red blood cells and plasma, have specific absorption spectra. The near-infrared light emitted from the photo emitter, which is absorbed and scattered when being reflected by the blood, is received by the photo detector. The light absorption and scattering coefficient is analyzed based on the intensity of the light detected by the photo detector and thereby used to calculate the hematocrit value.

When the hematocrit value obtained as above becomes higher than the specific value for the patient, the patient may suffer blood pressure drop and shock as presented in the description of the background technology. Therefore, the hematocrit value can be used as an index that reflects the condition of the patient receiving the water removal treatment (or other general blood treatments). In an embodiment of the present invention, ΔBV (the rate of change in the circulating blood volume) is calculated from the hematocrit value and used as an index that reflects the condition of the patient. ΔBV can be obtained by following equation:

$$\Delta BV = \frac{(Ht \text{ at the start of dialysis} - Ht \text{ at the time of measurement})}{Ht \text{ at the time of measurement}} \times 100$$

As shown in FIG. 1, the measuring means 12, which can consist of the hematocrit sensor 7, is connected electrically to the directing means 14. At the same time, the directing means 14 is connected electrically to the storing means 15 and to the controlling means 13.

This design is aimed at preventing the condition of the patient from becoming worse during water removal (or other general blood treatments) due to: the rise of the hematocrit value above the specific value for the patient, or the fall of ΔBV below the ΔBV value calculated from the hematocrit value at the start of blood treatment and the patient-specific hematotcrit value.

Storing means 15 records an ideal patient-specific blood parameter curve for the treatment duration. The storing means 15 can consist of memory or storage media (Floppy Disk (FD), Magneto-Optical (MO), or the like). The ideal hematocrit curve is obtained from ΔBV at various time intervals by monitoring in real time the hematocrit value of the patient subjected to water removal treatment before this dialysis treatment.

Further, in the water removal treatment (or other general blood treatments) carried out before this dialysis treatment, the hematocrit values are measured in real time. The ΔBV-water removal time curve is obtained by plotting the ΔBV values calculated from the hematocrit values on the vertical axis, and the water removal time on the horizontal axis. Additionally, it is preferable to obtain multiple curves and to choose the best curve (i.e., the curve in which the patient is in good condition and does not feel sick) as the specific blood parameter curve for that patient.

As described above, the ideal blood parameter curve for a specific patient reflects the good condition of the patient during water removal. Blood parameter curves other than the ΔBV-water removal time blood parameter curves may be included in the ideal blood parameter curve assessment. For example, a blood parameter curve that the attending physician decides to choose may be included. Accordingly, the ideal blood parameter curve is the curve that is most suitable for individual patient.

Figure 4:
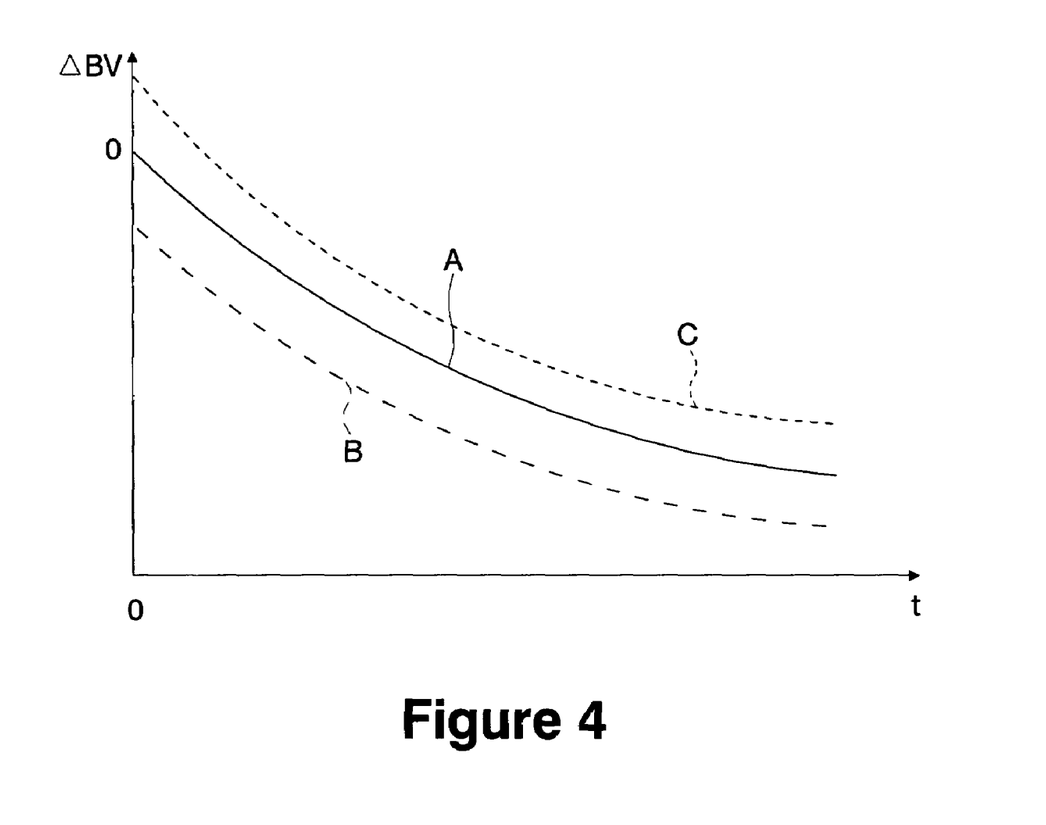
FIG. 4 is a graph showing the ideal blood parameter curve A, the lower limit curve B and the upper limit curve C recorded by the storing means to which the blood treatment device of the present invention is applied.

One example of the ideal blood parameter curve for a specific patient is shown as curve A in FIG. 4. Usually, with continuing water removal, the blood concentration in the body rises and the volume of circulating blood falls. An ideal blood parameter curve maintains the good condition of the patient and avoids the ΔBV value dropping to a level that induces shock even though the ΔBV must be lowered during continued water removal. This is the reason why the curve in FIG. 4 falls with time. However, in some patients the curves may take other forms (e.g., almost flat). In this embodiment, the ideal blood parameter curve for the individual patient, curve A, is obtained.

The ideal blood parameter curve A can be recorded by the storing means 15 by registering the raw data from the water removal treatment carried out before this dialysis treatment. More preferable is to record an approximation equation obtained by approximation processing (curve fitting) of the data. Specifically, the approximation equation is obtained from the ideal blood parameter curve of the water removal treatment carried out before this dialysis treatment through a calculation method (not shown in the figure), and the approximation equation is recorded by the storing means 15.

For example, the approximation equations can be:

$$\Delta BV = at^2 + bt + c$$

where t is the water removal time and a, b, and c are variable numbers including 0;

$$\Delta BV = b(1 - a^{(t/T)})$$

where T is planned water removal time, t is water removal time, and a and b are variable numbers;

$$\Delta BV = a(Ln(t))^2 + b(Ln(t)) + c$$

where t is water removal time and a, b, and c are variable numbers including 0. The approximation equations can also include other equations modified by the physician.

With the aforementioned method, the amount of data in the storing means 15 can be reduced, and the comparative calculation by the directing means 14 can be carried out smoothly and quickly. Also, the ideal blood parameter curve A can be calibrated easily, and the water removal rate suitable for the day-to-day conditions of the patient can be obtained. Examples of the approximation equations are explained later.

Directing means 14 compares the ideal blood parameter curve A recorded in the storing means 15 (FIG. 4) with ΔBV (more precisely, ΔBV obtained from the hematocrit value measured by the hematocrit sensor 7), and directs the controlling means 13 to change the control so that the ΔBV is more approximate to the ideal blood parameter curve A. Particularly, a lower limit curve which is lower than the ideal blood parameter curve by a predetermined value (the lower limit curve B) and an upper limit curve which is higher than the ideal blood parameter curve by another predetermined value (the upper limit curve C) are established. When ΔBV, which is calculated from the hematocrit value measured by the hematocrit sensor 7, reaches the lower limit curve B during blood treatment, the controlling means 13 is directed to change the control and lower or stop the water removal by the ultrafiltration pump 8 (treating means 11). As mentioned above, the water removal rate is set to be constant at the start of the treatment.

On the other hand, when ΔBV reaches the upper limit curve C during blood treatment, the controlling means 13 is directed to change the control and increase the water removal rate by the ultrafiltration pump 8 (treating means 11). By the control mentioned above, the ΔBV value always remains between the lower limit curve B and the upper limit curve C. This control can prevent worsening of the patient's condition caused by the water removal rate being too fast, as well as prolonging of the treatment duration caused by the water removal rate being too slow.

The degrees of deviation of the lower limit curve B and the upper limit curve C from the ideal blood parameter curve A can be the values that physicians have obtained from their experience. In that case, the deviation can be a standard value set for average patients or can be reset for each water removal treatment. It is preferable to obtain beforehand and to record to the storing means 15 the data regarding the relationship between the worsening of the patient condition and the degree of the lower deviation from the ideal blood parameter curve A. When the lower limit curve B is set based upon such lower deviation data, the individual patient can receive the best water removal treatment.

In the aforementioned embodiment, the water removal rate is changed when $\Delta BV$, which is calculated from the hematocrit value measured by the hematocrit sensor 7, reaches the lower limit curve B or the upper limit curve C. Alternatively, the change of control by the controlling means 13 can be based upon the degree of deviation of $\Delta BV$ from the ideal blood parameter curve A.

Specifically, the directing means 14 is designed to recognize the degree of deviation of the measured $\Delta BV$ from the ideal $\Delta BV$ and to control the ultrafiltration pump 8 based on that degree of deviation. This method of water removal rate control can provide a more finely regulated control to the specific patient than the method of controlling the water removal rate by changing the control at the time when the water removal rate reaches the lower or upper limit curve.

In the embodiment of this invention, the hematocrit sensor 7 is connected along the arterial blood circuit 1a. However, it is possible to connect the sensor along the venous blood circuit 1b. In this case, the arterial hematocrit value (Hta) needs to be estimated from the measured venous hematocrit value (Htv) by calculation, an example of which is shown below.

The relationship between arterial and venous hematocrit values is represented by the following equation:

$$Htv = \frac{Qb}{(Qb - Qu)} \times Hta \quad \text{Therefore,} \quad Hta = \frac{(Qb - Qu)}{Qb} \times Htv$$

In the arterial blood circuit 1a, the blood flow rate (Qb) and the water removal rate (Qu) are known, and the venous hemacrit value (Htv) can be measured. Therefore, the arterial hematocrit value (Hta) can be calculated. The $\Delta BV$ value is calculated based on the calculated hematocrit value (Hta), and the ideal blood parameter curve A is thus obtained.

The aforementioned blood treatment device can be used to treat an individual patient at the most suitable water removal rate because when the patient is treated by the treating means 11 (i.e., water removal), the controlling means 13 modulates the control so that the blood parameter ($\Delta BV$) measured by the measuring means 12 approximates to the ideal patient-specific blood parameter curve A, which has been obtained beforehand for the treatment duration.

The blood treatment device related to another embodiment includes the ultrafiltration pump 8 as a treating means 11, the hematocrit sensor 7 as a measuring means 12, a controlling means 13, a directing means 14, and a storing means 15. These elements are all electrically connected as shown in FIG. 1, wherein the ideal blood parameter curve recorded in the storing means 15 is calibrated by the target $\Delta BV$ value, which is calculated from the target hematocrit value and the starting hematocrit value, as measured by the hematocrit sensor 7.

For example, the ideal blood parameter curve is recorded in the storing means 15 as an approximation equation (approximated as described above), and is calibrated by changing the variables based on the hematocrit value at the start of measurement. The daily changing condition of the specific patient can be managed using these procedures while the blood treatments are carried out.

The hematocrit value of the patient at the start of the blood treatment is variable depending on the patient's food intake since the previous dialysis blood treatment, and sweating by the patient. Therefore, a hematocrit value that is a little lower than that expected to induce shock in the patient, is recorded as a target value in the blood treatment device (target $\Delta BV$). The target $\Delta BV$, which should be changed during the dialysis, is calculated from the hematocrit value obtained at the start of the measurement. The calibration can be performed by comparing this start value with the predicted changing rate of $\Delta BV$ at the end of the dialysis treatment using the approximation equation of the ideal blood parameter curve, which is recorded as the standard.

For example, the target $\Delta BV$ can be calculated by the following equation:

$$\text{target } \Delta BV = \left(\frac{\text{starting hematocrit value}}{\text{pre-set hematocrit value}} - 1\right) \times 100$$

Further, as another calibration method, if the calculated $\Delta BV$ value is equal to x times the predicted $\Delta BV$ of the recorded ideal blood parameter curve, the ideal blood parameter curve can be multiplied x times towards the horizontal axis.

Briefly, the calibration of the approximation equation related to the ideal blood parameter curve can be performed automatically, because the starting and end points on the $\Delta BV$-water removal time (t) graph are determined by pre-setting the end of measurement target $\Delta BV$ at the start of the measurement. Further, the calibration method is not restricted to this embodiment of the invention. Other methods that calibrate the ideal blood parameter curve based on the $\Delta BV$ at the start of the measurement can be used.

The blood treatment device related to another embodiment of the present invention, like the first embodiment described, includes the ultrafiltration pump 8 as a treating means 11, the hematocrit sensor 7 as a measuring means 12, a controlling means 13, a directing means 14, and a storing means 15 all electrically connected as shown in FIG. 1. $\Delta BV$ is calculated from the data from the hematocrit sensor 7, monitored, and approximated to the patient's specific ideal blood parameter curve recorded in the storing means 15.

Figure 5:
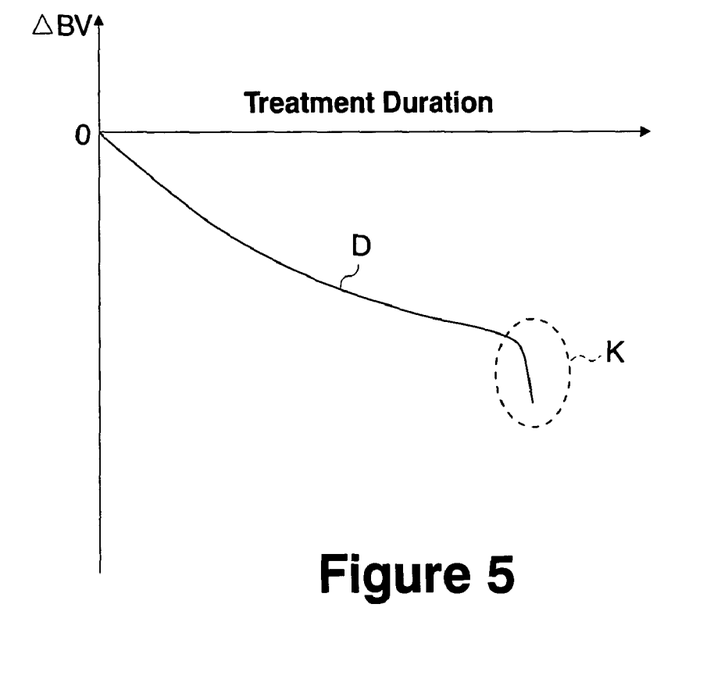
FIG. 5 is a graph showing the measured curve D in a blood treatment device of the present invention.

Particularly, the horizontal axis of the ideal blood parameter curve represents the treatment duration and the vertical axis represents $\Delta BV$. The ideal blood parameter curve is obtained beforehand and the directing means 14 directs the controlling means 13 to control the rate of water removal by the ultrafiltration pump 8 in such a way that $\Delta BV$ calculated from the data from the hematocrit sensor 7 approximates to the ideal blood parameter curve. More particularly, the curve of the measured $\Delta BV$ (designated as the measured curve D), which is shown in FIG. 5 as a treating time vs. $\Delta BV$ graph, is monitored. The slope of each time point on the measured curve $$D\left(\Delta\left(\frac{\Delta BV}{\Delta t}\right)\right)$$

is obtained in real time. The slope is the variable ratio of the measured curve D.

When the variable ratio of the measured curve D drops abruptly (the drop such as in the range identified as K in FIG. 5) or rises, it is feared that ΔBV might exceed the pre-set upper limit curve or drop below the pre-set lower limit curve in a short time. In such a situation, the control by the ultrafiltration pump 8 may not be able to follow. Therefore, in the present embodiment, a permissible range of the variable ratio (limiting variable ratio) of the measurement curve D is predetermined wherein if the variable ratio of the measured curve D goes over the limiting variable ratio, an alarm sounds to warn the attending physicians and staff that there is a change in the patient's condition. At the same time, the ultrafiltration pump 8 is stopped.

This controlling means can respond to sudden changes in the measurement curve D, thereby improving the safety of the patient and reducing the workload for the attending physicians and staff monitoring the measurement curve D. Such sudden changes cannot be handled by the treating means 11 (the ultrafiltration pump 8) via the directing means 14. Presently, an embodiment of this invention indicates that the treating means 11 can be the ultrafiltration pump 8, but when the measured curve D changes abruptly, development of the low blood pressure syndromes of the patient should be avoided as much as possible by for example, giving substitution fluid from the fluid substitution unit. More particularly, when the blood parameters measured by the hematocrit sensor 7 change abruptly, the abrupt change can be suppressed by overriding the direction from the directing means 14 (i.e., the direction to the controlling means 13 to change the control to approximate the measured hematocrit value to the ideal blood parameter curve).

The blood treatment device related to another embodiment of the present invention, like the first embodiment described, includes the ultrafiltration pump 8 as a treating means 11, the hematocrit sensor 7 as a measuring means 12, a controlling means 13, a directing means 14, and a storing means 15 all electrically connected as shown in FIG. 1. ΔBV is calculated from the data from the hematocrit sensor 7, monitored, and approximated to the patient's specific ideal blood parameter curve recorded in the storing means 15.

In the present embodiment, both the control of ΔBV as a measured value to approximate to the ideal blood parameter curve and the treatment duration (dialysis time or water removal time) are taken into consideration. Particularly, when the upper limit of the water removal rate pre-set for each patient is A, the deviation of the measured ΔBV from the standard ΔBV (the value on the ideal blood parameter curve) is C. The value of C at which the water removal should be stopped is C0, which is set differently for each patient. Then, B is A, if C is less than $$(1-A) \times C0; B \text{ is } -\left(\frac{C}{C0}\right)+1,$$

if C is more than $(1-A) \times C$, but less than C0; and B is 0, if C is greater than C0.

Figure 6:
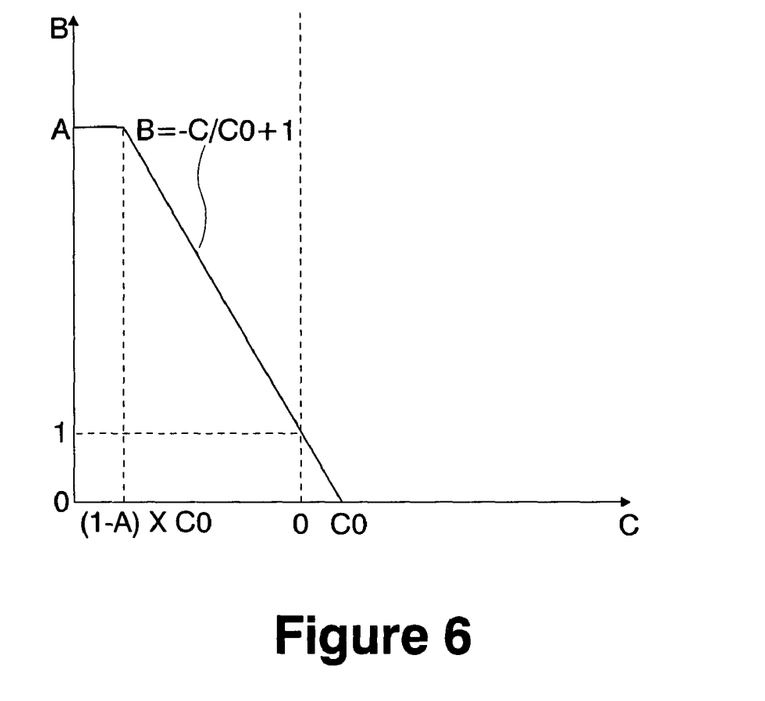
FIG. 6 is a graph showing the C-B relationship in a blood treatment device of the present invention.

FIG. 6 shows a graph with C as the horizontal axis and B as the vertical axis and demonstrates the changing of B. When the total time for the treatment (dialysis or water removal) is T, the water removal rate at time t is V. The remaining time for the treatment is (T−t) and the remainder of the water to be removed is U. Then, V=B×Vf where $$Vf = \frac{U}{(T-t)}.$$

Figure 7:
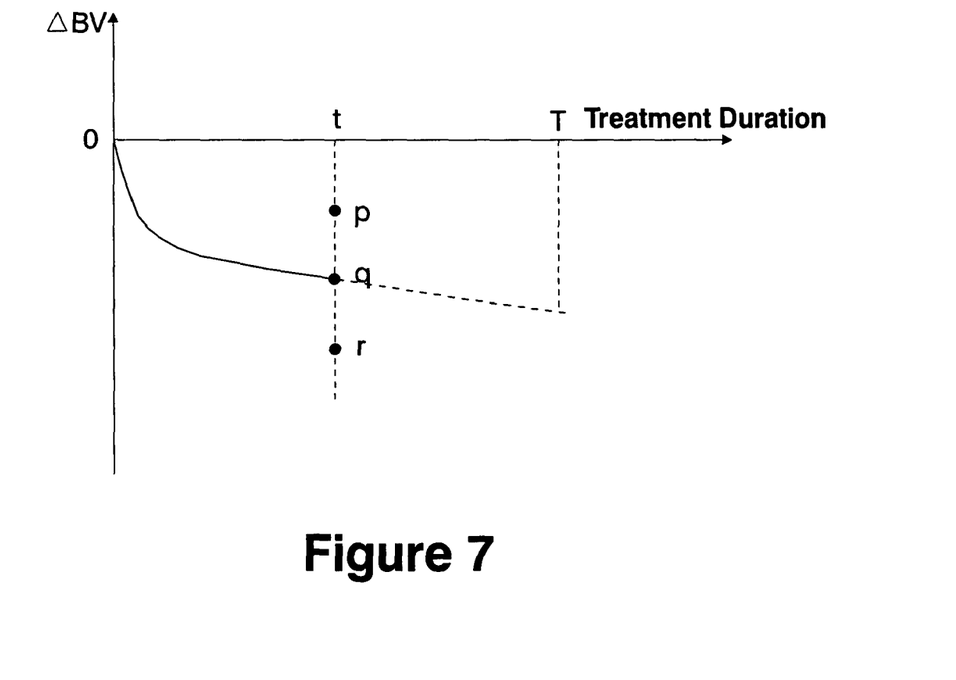
FIG. 7 is a graph showing ΔBV at the treatment duration time t.

From these equations, if the measured value of ΔBV at t=the standard ΔBV (i.e., if the measured value of ΔBV is q in FIG. 7), then $$V = Vf = \frac{U}{(T-t)}.$$

Also, B=1 because C=0 in FIG. 6. Therefore, if the measured value changes along the ideal blood parameter curve, the planned amount of water removal can be attained with the end of the treatment.

If the measured value of ΔBV at t>the standard ΔBV (i.e., if the measured value of ΔBV is p in FIG. 7), then V>Vf and the measured value of ΔBV changes toward the approximation to the standard value ΔBV on the ideal blood parameter curve. If the measured value of ΔBV at t<the standard ΔBV (i.e., if the measured value of ΔBV is r in FIG. 7), then V<Vf. Even in this last case, the measured value of ΔBV changes toward the approximation to the standard value ΔBV on the ideal blood parameter curve.

The more the measured ΔBV changes toward the approximation of the standard value ΔBV of the ideal blood parameter curve, the closer the water removal rate V goes to Vf. Also, the time to reach the planned amount of water removal is closer to the treatment duration T. However, because of the limitation that the water removal rate V is more than 0 but less than (A×Vf), the measured ΔBV may never reach the standard ΔBV on the ideal blood parameter curve. In this case, following procedures may be carried out. When the remainder of the treating time (T−t) becomes TR, the approximation to the ideal blood parameter curve is terminated. After that, the water removal is carried out at a constant speed of $$V = \frac{UR}{TR}$$

(the remainder of water to be removed at this time is UR). Thus, the planned amount of water removal may be attained forcefully. TR may be set for individual patients.

Figure 8:
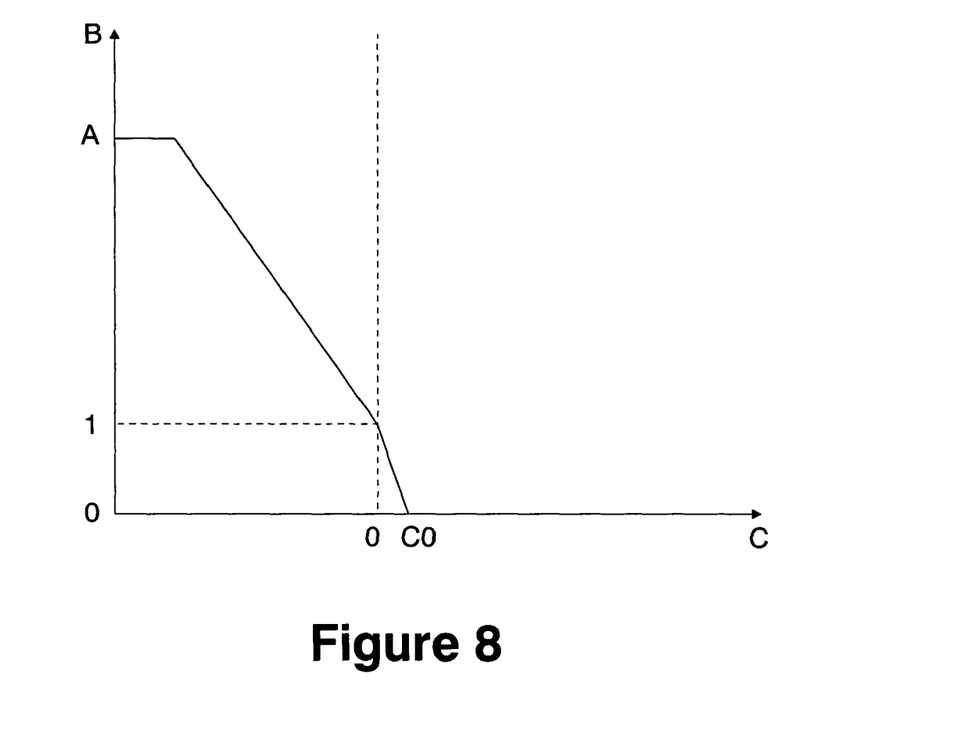
FIG. 8 is a graph showing another C-B relationship in a blood treatment device of the present invention.

Further, the graph shown in FIG. 6 is a straight line with a constant slope when C is greater than (1−A)×C0 and less than C0. It may be set so that the slope when C is greater than 0 may be greater than that when C is greater than (1−A)×C0 and less than C0 as an example shown in FIG. 8. Through these procedures, the slow down of the water removal rate can be accelerated when the measured value of ΔBV is lower than the standard ΔBV.

Figure 9:
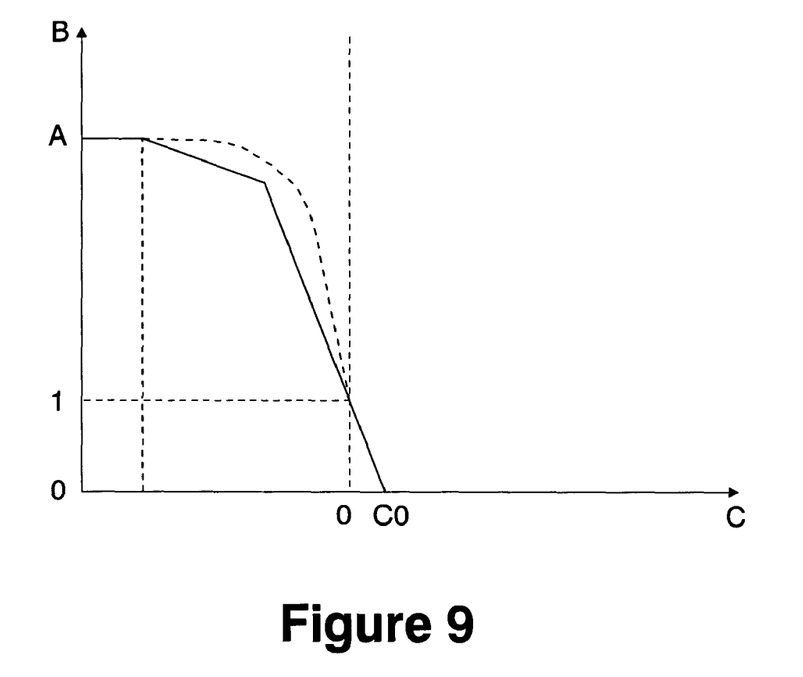
FIG. 9 is a graph showing another C-B relationship in a blood treatment device of the present invention.

Still further, when C is in the range of below 0, the slope can be changed as shown in FIG. 9. In this case, when the measured value of ΔBV is much greater than the standard ΔBV, the increase of the water removal rate can be suppressed and the burden to the patient can be reduced. It is also possible to make the line curved (shown in FIG. 9 as a dotted line) or the line graphed with more than three breaking points (not shown) when C is less than 0.

On the other hand, the water removal rate may be obtained from the equation V=B×Vf×α, which is derived from V=B×Vf where $$Vf = \frac{U}{(T-t)},$$

by applying a variable α. The α is based upon time or the water removal completion rate and is usually set to be 1, wherein the regular equation is used. However, when the water removal rate is high (for example, around the start of the treatment) or the water removal completion rate is low, a can be greater than 1 in order to accelerate the water removal rate.

Particularly, by applying the variable a to the regular equation, the equation becomes dependent on time or on the water removal completion rate. More particularly, the upper limit of the water removal rate V in the equation should not exceed the value when α=1 and B=A. It is also possible to set the upper limit separately.

By this embodiment, the blood treatment and the water removal treatment are finished almost at the same time because the difference between the measured blood parameter and the standard, the treatment duration, and the remainder of the water removal are all taken into consideration. Accordingly, the burden on attending physicians and staff as well as treatment costs due to extended treatment durations are reduced. Since the water removal time is shorter than the treatment duration, reverse ultrafiltration can be avoided.

The blood treatment device related to another embodiment of the present invention, like the first embodiment described, includes the ultrafiltration pump 8 as a treating means 11, the hematocrit sensor 7 as a measuring means 12, a controlling means 13, a directing means 14, and a storing means 15 all electrically connected as shown in FIG. 1. ΔBV is calculated from the data from the hematocrit sensor 7, monitored, and approximated to the patient's specific ideal blood parameter curve recorded in the storing means 15.

Figure 10:
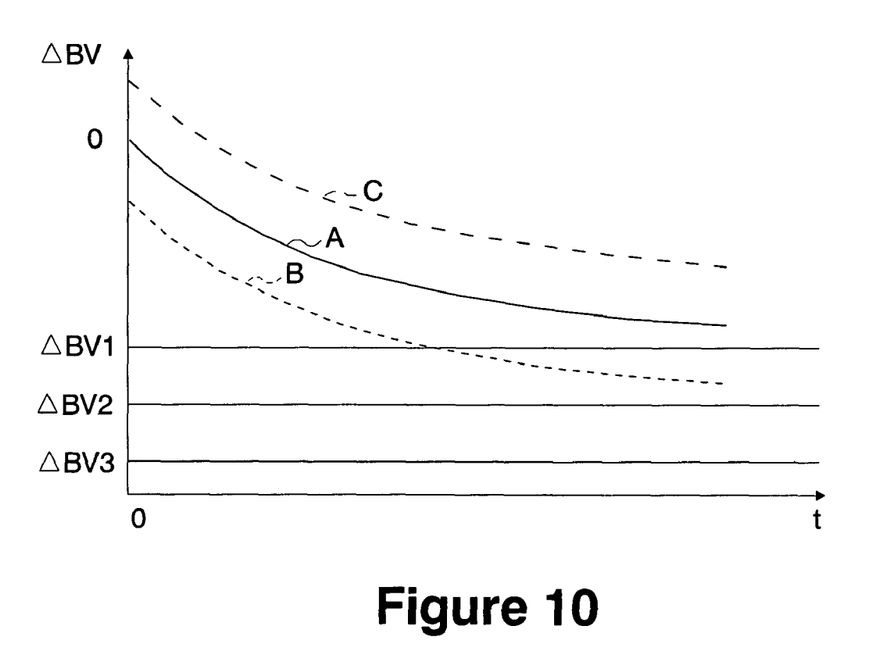
FIG. 10 is a graph showing the ideal blood parameter curve, the lower limit curve and the upper limit curve with the predetermined lines in a blood treatment device of the present invention.

In this embodiment, in addition to the lower limit curve B and the upper limit curve C, the predetermined lines for ΔBV (ΔBV1, ΔBV2, and ΔBV3) are established as shown in FIG. 10. These predetermined lines are in parallel with the time axis, and when the measured ΔBV is below one of the predetermined lines, the water removal rate is controlled according to the pre-set value overriding the control of approximating the measured ΔBV to the standard ΔBV on the ideal blood parameter curve. When the measured ΔBV falls below the predetermined line, control is performed to provide a water removal rate that corresponds to the predetermined line.

When the measured ΔBV falls abruptly below the lower limit curve B due to the physical condition of the patient or other reasons, the water removal rate is changed (usually the water removal rate is lowered or stopped) by further lowering ΔBV below the predetermined line. Therefore, even if the water removal rate is uncontrollable by the controlling means, because of the abrupt drop in the measured ΔBV, the water removal condition is changed such that the safety for the patient is improved.

In this embodiment of the present invention, three predetermined lines (ΔBV1, ΔBV2 and ΔBV3) are established. However, it may be possible to establish one or two or more than four predetermined lines. In FIG. 10, ΔBV1 is established across the lower limit curve B, but it may alternatively be established across the upper limit curve C.

Further, when the measured ΔBV reaches any one of the predetermined lines, the pre-set water removal control is activated and an alarm may sound. Another warning system, other than a sounding alarm, may also be installed to alert attending physicians and staff. Of course, an alarm or a warning system for physicians and staff without the water removal control may be installed as well.

Still further, when the measured ΔBV falls below any of the predetermined lines and the rate of water removal is changed or the measured ΔBV rises above the predetermined line, the patient's condition improves and the water removal rate automatically returns to normal. Alternatively, the fact that the measured ΔBV rose to a normal level is reported to the attending physicians and, after confirmation by the physicians that the patient condition is improved, the water removal rate may then be manually returned to a normal level.

Although an embodiment of the invention is explained as above, the present invention is not restricted to this embodiment. For example, the dialyzer and the blood circuit applicable to this invention may comprise another arrangement. The dialyzer in the above embodiment of the invention is a central system that includes two separate components: the dialyzing fluid supplier and the dialysis monitor. However, the present invention may be applied to a system in which the two components are combined in a so-called personal dialysis apparatus.

In an embodiment of the present invention, dialyzing fluid is supplied to the dialyzer 2 by the duplex pump P in the dialysis monitor 6. However, dialyzing fluid may also be supplied using a balancing chamber wherein the duplex pump is not used. Further, a double needle consisting of the arterial and the venous needles were used in the blood circuit, but a single needle may be employed instead.

Additionally, the hematocrit sensor in the present invention is not restricted to use in dialysis treatment, but can also be applied to various other blood purifying apparatuses that require extracorporeal blood circulation. In these cases, the blood can flow through not only flexible tubing but also various circuits as well. In an embodiment of the present invention, ΔBV, which is calculated from the hematocrit value, is used as the blood parameter. However, the hemtocrit value itself (or other data that reflect the condition of the patient) may be used as the blood parameter.

In a present embodiment, the treating means 11 is the ultrafiltration pump 8, which controls the rate of water removal. The present invention is not limited to this treating means. Rather, the treating means 11 can be the driving means for the blood circuit 1, the dialysis monitor 6, and the dialyzing fluid supplier. Also, the controlling means 13 is the controller for the driving means. For example, when the treating means 11 is the blood pump 3, which is installed in the blood circuit 1, the blood flow rate may be controlled by the blood pump 3 in such a way that the measured ΔBV approximates to the ideal blood parameter curve.

To approximate the measured ΔBV to the ideal blood parameter curve, the rates of water removal and blood flow are controlled. In addition, one of the following, or a combination of two or more, may be controlled: rate of fluid substitution, concentration of dialyzing fluid, sodium ion concentration, blood treatment duration, flow rate of dialyzing fluid, temperature of dialyzing fluid, volume of substitution fluid, and amount and rate of drug injected. Particularly, the directing means 14 may direct the change in the pre-set controls of the above.

The individual patient can receive the most suitable blood treatment with reduced treatment duration by one embodiment of the present invention when an ideal patient-specific blood parameter curve for the treatment duration is obtained beforehand, and when the patient is treated by the treating means using the set treatment procedures. The controlling means changes the control so that the blood parameters measured by the measuring means approximate to the ideal blood parameter curve.

The individual patient can receive the most suitable blood treatment by another embodiment of the present invention when the blood parameter is the hematocrit value, which reflects the concentration of blood or the rate of circulating blood volume change as calculated from the hematocrit value. In this manner, the condition of the patient can be monitored more reliably.

More effective approximation to the ideal blood parameter curve for an individual patient can be achieved by yet another embodiment of the invention, wherein the treating means comprises a driving means of a blood purifying apparatus that purifies the blood of a patient while extracorporeally circulating the blood. The change in the treatment procedures in the controlling means changes one of, or a combination of two or more of, the following: water removal rate; blood flow rate; fluid substitution rate; concentration of dialyzing fluid; sodium ion concentration; time for blood treatment; flow rate of dialyzing fluid; temperature of dialyzing fluid; volume of substitution fluid; amount of drug injected; rate of drug injection.

The daily changing condition of the individual patient can managed promptly by yet another embodiment of the invention, wherein the ideal blood parameter curve is corrected based on the blood parameters at the start of measurement by the measuring means.

The most suitable and finer control for the individual patient can be achieved by still another embodiment of the invention, wherein the change in control by the controlling means is based on the deviation of the blood parameters, as measured by the measuring means, from the ideal blood parameter curve.

The comparative calculation of the measured blood parameter and the ideal blood parameter curve can be carried out smoothly and quickly by another embodiment of the invention, wherein the ideal blood parameter curve is an approximation equation.

The abrupt change in the measured blood parameter, which the treating means cannot control, can be managed according to another embodiment of the invention. In this embodiment, the safety to the patient can be improved and the work load of the attending physicians and staff with respect to monitoring the blood parameter can be reduced. Here, when the blood parameters measured by the measuring means undergo an abrupt change, the control toward suppressing the change is carried out by overriding the control to approximate to the ideal blood parameter curve.

The blood treatment and the water removal treatment can be completed at approximately the same time, because another embodiment of the invention considers both the deviation of the measured value of the blood parameter from the standard value and also the treatment duration and the remainder of the water to be removed. In this embodiment, the treatment duration is one of the parameters to approximate to the ideal blood parameter curve. The cost of the medical treatments and the work load for the physicians and staff are reduced, because the treatment duration is shorter and the reverse ultrafiltration, due to the water removal time being shorter than the treatment duration, can be avoided.

The patient's safety can be improved by the another embodiment of the invention, wherein the absolute base line was established against the blood parameters. When the blood parameters drop below the base line, the treating means is controlled by overriding the control to approximate to the ideal blood parameter curve.

Although the present invention has been described in connection with certain embodiments set forth above, it is not limited to such embodiments, but rather is defined by the scope of the claims appended hereto.

We claim:

1. A blood treatment device comprising:
   a treating unit configured to perform a predetermined treatment to blood collected from a patient;
   a measuring unit configured to measure at least one blood parameter and to indicate a status of said blood of said patient;
   a controlling unit configured to control at least one treatment condition based on said blood parameter measured using said measuring unit;
   a storing unit configured to store an ideal patient-specific blood parameter curve for a specific treatment duration, said ideal patient-specific blood parameter curve being obtained based on said blood parameter that is measured in real time in a blood treatment for said patient prior to said predetermined treatment of said patient; and
   a directing unit configured to compare said ideal patient-specific blood parameter curve stored in said storing unit with said blood parameter measured with said measuring unit, and to adjust a control from said controlling unit so that said measured blood parameter approximate to said ideal patient-specific blood parameter curve.

2. The blood treatment device of claim 1, wherein said blood parameter is a hematocrit value indicating either a blood concentration or a rate of change in a circulating blood volume derived from said hematocrit value.

3. The blood treatment device of claim 1 wherein:
   said treating unit is provided with a driving unit for a blood purifying apparatus configured to purify said blood of said patient while extracorporeally circulating said blood; and
   said at least one treatment condition controlled by said controlling unit is selected from the group consisting of a water removal rate, a blood flow rate, a fluid substitution rate a concentration of a dialyzing fluid, a sodium ion concentration a blood treatment duration, a flow rate of a dialyzing fluid, a temperature of a dialyzing fluid, a volume of a substitution fluid, an amount of a drug injected, and a rate of a drug injection.

4. The blood treatment device of claim 1, wherein said ideal patient-specific blood parameter curve is corrected based on said blood parameter measured by said measuring unit at a start of said predetermined treatment.

5. The blood treatment device of claim 1, wherein said directing unit adjusts said control of said controlling unit based on a deviation between said ideal patient-specific blood parameter curve and said blood parameter measured by said measuring unit.

6. The blood treatment device of claim 1, wherein said ideal patient-specific blood parameter curve stored in said storing unit is an approximation equation calculated from said ideal patient-specific blood parameter curve obtained from said blood treatment to said patient prior to said predetermined treatment to said patient.

7. The blood treatment device of claim 1, wherein, when said blood parameter measured by said measuring unit undergoes an abrupt change, a direction to adjust from said directing unit is overridden in such a way as to suppress said abrupt change.

8. The blood treatment device of claim 1, wherein said at least one blood parameter includes said specific treatment duration.

9. The blood treatment device of claim 1, wherein:
an absolute base line is established against said blood parameter; and
said control adjusted by said directing unit is overridden when said blood parameter falls below said absolute base line.

10. A blood treatment method using a blood treatment device, comprising:
performing a predetermined treatment to blood collected from a patient;
measuring at least one blood parameter and indicating a status of said blood of said patient;
controlling at least one treatment condition based on said blood parameter measured in said measuring;
obtaining an ideal patient-specific blood parameter curve that is specific to a treatment duration considered ideal for said patient and that is based on said blood parameter measured in real time in a blood treatment to said patient prior to said predetermined treatment to said patient; and
directing to adjust said controlling when said predetermined treatment for said patient is performed in said performing, so that said blood parameter measured in said measuring approximate said ideal patient-specific blood parameter curve.

11. The blood treatment method of claim 10, wherein said blood parameter is a hematocrit value indicating either a blood concentration or a rate of change in a circulating blood volume derived from said hematocrit value.

12. The blood treatment method of claim 10, wherein:
said performing includes driving a blood purifying apparatus configured to purify said blood of said patient while extracorporeally circulating said blood; and
said at least one treatment condition controlled in said controlling is selected from the group consisting of a water removal rate, a blood flow rate, a fluid substitution rate, a concentration of a dialyzing fluid, a sodium ion concentration, a blood treatment duration, a flow rate of a dialyzing fluid, a temperature of a dialyzing fluid, a volume of a substitution fluid, an amount of a drug injected, a rate of a drug injection.

13. The blood treatment method of claim 10, wherein said ideal patient-specific blood parameter curve is corrected based on said blood parameter measured in said measuring at a start of said predetermined treatment.

14. The blood treatment method of claim 10, wherein, in said directing, said controlling is adjusted based on a deviation between said ideal patient-specific blood parameter curve and said blood parameter measured in said measuring.

15. The blood treatment method of claim 10, wherein, when said blood parameter measured in said measuring undergoes an abrupt change, a direction to adjust in said directing is overridden in such a way as to suppress said abrupt change.

16. The blood treatment method of claim 15, wherein said direction is overridden by said controlling, which adjusts to approximate a hematocrit value, measured as said blood parameter in said measuring, to the ideal patient-specific blood parameter curve.

17. The blood treatment method of claim 10, wherein, said at least one blood parameter includes said treatment duration when said controlling is adjusted in said directing.

18. The blood treatment method of claim 10, wherein:
an absolute base line is established against said blood parameter; and
a direction to adjust in said directing is overridden when said blood parameter falls below said absolute base line.

19. The blood treatment method of claim 18, wherein said direction is overridden by said controlling, which changes the direction to approximate a hematocrit value, measured as said blood parameter in said measuring, to the ideal patient-specific blood parameter curve.

* * * * *